United States Patent [19]

Nomura et al.

[11] Patent Number: 5,750,537
[45] Date of Patent: May 12, 1998

[54] USE OF 5HT$_3$ ANTAGONIST TO TREAT IMPOTENCE

[75] Inventors: Kazuhiko Nomura, Tsukuba; Isamu Yamaguchi, Kawanishi, both of Japan

[73] Assignee: Fujisawa Pharmaceutical Co., Ltd., Osaka, Japan

[21] Appl. No.: 793,798

[22] PCT Filed: Aug. 31, 1995

[86] PCT No.: PCT/JP95/01745

§ 371 Date: Mar. 17, 1997

§ 102(e) Date: Mar. 17, 1997

[87] PCT Pub. No.: WO96/09069

PCT Pub. Date: Mar. 28, 1996

[30] Foreign Application Priority Data

Sep. 19, 1994 [JP] Japan ..................... 6-251521

[51] Int. Cl.$^6$ .................... A61K 31/44; A61K 31/415
[52] U.S. Cl. ............................ 514/304; 514/397
[58] Field of Search ........................... 514/304, 397

[56] References Cited

U.S. PATENT DOCUMENTS

| 4,695,578 | 9/1987 | Coates et al. ............... 514/397 |
| 4,914,107 | 4/1990 | Cohen et al. ............... 514/288 |
| 5,141,945 | 8/1992 | Kato et al. . |
| 5,173,493 | 12/1992 | Kato et al. . |
| 5,290,785 | 3/1994 | Kato et al. . |
| 5,300,645 | 4/1994 | Audia et al. ............... 546/49 |
| 5,607,938 | 3/1997 | Katsuta et al. . |

OTHER PUBLICATIONS

U.S. application No. 08/736,248, filed Oct. 24, 1996, Pending.

U.S. application No. 08/793,798, filed Mar. 17, 1997, Pending.

*Primary Examiner*—Marianne M. Cintins
*Assistant Examiner*—M. Moezie
*Attorney, Agent, or Firm*—Oblon, Spivak, McClelland, Maier & Neustadt, P.C.

[57] ABSTRACT

An impotence remedy containing a 5HT$_3$ antagonist as the active ingredient.

1 Claim, No Drawings

1

USE OF 5HT₃ ANTAGONIST TO TREAT IMPOTENCE

This Application is a 371 of PCT/JP95/01745 filed Aug. 31, 1995.

TECHNICAL FIELD

The present invention relates to a therapeutic agent for impotence which comprises a $5HT_3$ antagonist as the active ingredient, and is useful in the medical field.

BACKGROUND ART

5HT receptors are classified into the subtypes of $5HT_1$, $5HT_2$, $5HT_3$, $5HT_4$, $5HT_5$, $5HT_6$ and $5HT_7$ (see D. Hoyer et al., Pharmacol. Rev., 1994 in press; P.P.A. Humphrey et al., Trends Pharmacol. Sci., 14, 233, 1993).

It is reported that 5HT1 receptors are densely distributed in smooth muscle, cerebral cortex, hippocampus, ventral horn of spinal cord, basal ganglia, etc., and are involved in the depression of nervous system and in the modulation of cardiovascular system (e.g., hypotension, tachycardia, dilation and contraction of vascular smooth muscle) and so on;

that $5HT_2$ receptors are densely distributed in smooth muscle, motor cortex, etc., and are involved in the depolarization of motor nerve, modulation of body temperature, hypertension, vasoconstriction and the contraction of smooth muscle in digestive tract, trachea and vesica; and that $5HT_3$ receptors are densely distributed in both peripheral and central nervous system including human cerebral cortex, etc., and are involved in the expression of emesis and the attack of hemicrania (see A.H Dickenson's review on 5HT).

Recently, the need for a therapeutic agent for impotence has been growing clinically. Although there is a therapeutic method for impotence in which vasoactive drugs such as papaverine or PGE1 are injected directly in corpus cavernosum, this method is not desirable because of some undesirable side effects or the methodology. Consequently, the development of an effective oral therapeutic agent for impotence has been needed. Up to the present, however, the effects of conventional oral drugs which were considered to be beneficial for impotence has been proved to be unsatisfactory, because of their poor efficacy, their safety, or undesirable side effects.

It has been reported that 5HT (serotonin) is involved in the expression of sexual behavior (see Gessa GL, Tangliamonte A, In Sexual Behavior, Pharmacology and Biochemistry, edited by Sandler Mand, Gessa GL, New York; Raven Press, 1975). On the other hand, regarding the relationship between $5HT_3$ receptors and sexual behavior, it is reported that $5HT_3$ antagonist had no effect on sexual behavior in normal (non-stressed) animals (see Stoessl AJ et al., Brain Res. 517, 111, 1990; Tanco SA et al., Experimentia 49, 238, 1991).

The object of the present invention is to provide a novel and effective medicine for the treatment of impotence.

DISCLOSURE OF THE INVENTION

We, the inventors of the present invention, found that a $5HT_3$ antagonist is effective for the treatment of impotence, and have completed the present invention on the basis of this finding.

Specifically, the present invention relates to a therapeutic agent for impotence which comprises a $5HT_3$ antagonist as an active ingredient.

2

The $5HT_3$ antagonist as referred to this invention includes a drug having a stronger antagonistic effect against $5HT_3$ receptors (for example, those existing in human cerebral cortex) than its antagonistic effect against $5HT_1$ receptors (for example, those existing in mouse ventral spinal marrow) and $5HT_2$ receptors (for example, those existing in human smooth muscle). The receptor antagonist is abbreviated as an antagonist in this invention.

Preferred examples of the $5HT_3$ antagonist are endo-1H-indole-3-carboxylic acid 8-methyl-8-azabicyclo[3.2.1]oct-3-yl ester(common name, Tropisetron), endo-3,5-dichlorobenzoic acid 8-methyl-8-azabicyclo[3.2.1]oct-3-yl ester(common name, Bemesetron), 1,2,3,9-tetrahydro-9-methyl-3-[(2-methyl-1H-imidazol-1-yl) methyl]-4H-carbazol-4-one·hydrochloride dihydrate (common name, Ondansetron), endo-1-methyl-N-(9-methyl-9-azabicyclo[3.3.1]non-3-yl) -1H-indazole-3-carboxamide (common name, Granisetron),(R)-5-[(1-methyl-3-indolyl)carbonyl]-4,5,6,7-tetrahydro-1H-benzimidazole·hydrochloride(common name, YM-060), (+)-8, 9-dihydro-10-methyl-7-[(5-methyl-1H-imidazol-4-yl) methyl]pyrido[1,2-a]indol-6(7H)-one·hydrochloride (common name, FK1052), (+)-3,4-dihydro-5-methyl-2-[1-(5-methyl-1H-imidazol-4-yl) ethyl] pyrimido[1,6-a]indol-1(2H)-one·hydrochloride (common name, FR), etc., which, however, are not limitative, but any other known or novel $5HT_3$ antagonists can be used in the present invention. For example, compounds disclosed in the following patent publications are known. European Patent Laid-Open No. 0189002A, European Patent Laid-Open No. 067770A, European Patent Laid-Open 0191562A, European Patent Laid-Open No. 0200444A, European Patent Laid-Open No. 0381422A, European Patent Laid-Open No. 0361317A, European Patent Laid-Open No. 0420086A.

The $5HT_3$ antagonist may include pharmaceutically-acceptable salts thereof. Pharmaceutically-acceptable salts are commonly used non-toxic salts, including, for example, inorganic acid salts (e.g., hydrochlorides, hydrobromides, sulfates, phosphates), organic acid salts(e.g., formates, acetates, trifluoroacetates, oxalates, maleates, fumarates, tartrates, methanesulfonates, benzenesulfonates, toluenesulfonates), alkali metal salts (e.g., sodium salts, potassium salts), alkaline earth metal salts (e.g., calcium salts), and salts with amino acids (e.g., arginine salts, aspartates, gultamates).

The known compounds which mentioned hereinabove as examples of the $5HT_3$ antagonist for use in the present invention can be prepared by the methods described in the above-mentioned publications or by any known methods.

Where the $5HT_3$ antagonist includes stereoisomers with asymmetric carbon atom(s), the individual stereoisomers and their mixtures are also within the scope of the $5HT_3$ antagonist for use in the present invention.

The $5HT_3$ antagonist can be administered orally, parenterally (including for intravenous injection, subcutaneous injection and intramuscular injection) or externally (locally), in any form of ordinary pharmaceutical preparations of, for example, capsules, microcapsules, soft capsules, tablets, granules, powdery preparations, powders, troches, pills, ointments, emulsions, suppositories, injections, liquids, suspensions, syrups, elixirs, or limonades. Wherein, preferred one is oral administration of the $5HT_3$ antagonist.

The pharmaceutical preparations mentioned above can be prepared by any ordinary methods using any ordinary organic and inorganic carriers known for formulation of medicines, for example, vehicles such as sucrose, starch, mannitol, sorbitol, lactose, glucose, cellulose, talc, calcium phosphate, calcium carbonate; binding agents such as cellulose, methyl cellulose, hydroxymethyl cellulose, polypropylpyrrolidone, gelatin, arabic gum, polyethylene glycol, sucrose, starch; disintegrators such as starch, carboxymethyl cellulose, hydroxypropyl starch, sodium hydrogencarbonate, calcium phosphate, calcium citrate; lubricants such as magnesium stearate, aerosil, talc, sodium laurylsulfate; flavorings such as citric acid, menthol, glycine, orange powder; preservatives such as sodium benzoate, sodium bisulfite, methylparaben, propylparaben; stabilizers such as citric acid, sodium citrate, acetic acid; suspending agents such as methyl cellulose, polyvinyl pyrrolidone, aluminium stearate; dispersants such as hydroxypropylmethyl cellulose; diluents such as water; base waxes such as cacao butter, white petrolatum, polyethylene glycol, etc. The amount of the active ingredient to be in the pharmaceutical preparations may be one that is sufficient for producing the intended curing effect, and, for example, may be from 0.001 µg/kg to 1 mg/kg for oral or parenteral administration.

The 5HT$_3$ antagonist may be administered, in general, with in a unit dose of from 0.05 µg/body to 50 mg/body once to four times a day. However, the above dose may be increased or decreased, depending on the age and the body weight and condition of the patient or on the administration route.

EXAMPLES

Now, the present invention is described in more detail herein under with reference to the following test example and example, which, however, is not intended to restrict the scope of the invention.

Test Example

Beneficial Effect of 5HT$_3$ Antagonists on Copulatory Disorder in Male Mice induced by Psychosocial Stress (1) Experimental Method:

Postpubertal male ICR mice (8 weeks) were individually housed and the isolation housing continued for 4 weeks. Then, they were confronted with estrus female mice and the copulatory behavior of male mice was measured for 10 minutes. The experiment was carried out under red dim illuminations. The control mice were group-housed for 4 weeks. The tested compounds described below were administered orally to the male mice one hour before the behavioral testing. Solvent (distilled water or 0.5% methyl cellulose solution) was administered to the vehicle-treated mice of isolated group (dose of 0 ug/kg). The frequency of copulatory elements (mounting and intromission) during the testing were measured and analyzed.

(2)Tested compounds:

Tropisetron, Bemesetron, Granisetron, Ondansetron, YM-060 and FK1052

(3) Experimental Results:

The beneficial effects of these six 5HT$_3$ antagonists on stress-induced copulatory disorder in male mice are shown in Table 1.

TABLE 1

Effects of 5HT$_3$ antagonists on Copulatory Disorder in Male Mice

| Group (number of mice tested) | Frequency of Copulatory Behavior in 10 Minutes' Testing [times]: Mean ± S.E. [Incidence, %] | |
|---|---|---|
| | Mounting | Intromission |
| Control Group (16) | 6.12 ± 1.07 [94] | 6.31 ± 1.87 [94$^\alpha$] |
| Tropisetron | | |
| 0 µg/kg (16) | 2.25 ± 0.50$^b$ [75] | 1.25 ± 0.39$^a$ [50] |
| 0.1 µg/kg (8) | 3.88 ± 1.09 [75] | 2.38 ± 0.91 [75] |
| 1 µg/kg (8) | 6.00 ± 1.31 [88] | 4.88 ± 1.29 [88] |
| 10 µg/kg (16) | 7.19 ± 1.45$^A$ [88] | 6.06 ± 1.19$^A$ [88] |
| Control Group (8) | 5.75 ± 0.73 [100] | 3.75 ± 1.00 [88] |
| Bemesetron | | |
| 0 µg/kg (8) | 1.88 ± 0.74$^b$ [63] | 1.25 ± 0.53$^a$ [63] |
| 1 µg/kg (8) | 4.88 ± 0.95 [100] | 3.12 ± 0.67 [88] |
| Control Group (10) | 5.80 ± 1.47 [70] | 4.80 ± 1.40 [70] |
| Granisetron | | |
| 0 µg/kg (10) | 1.30 ± 0.60 [40] | 0.90 ± 0.43$^a$ [40] |
| 0.1 µg/kg (10) | 3.30 ± 1.07 [60] | 2.80 ± 0.96 [60] |
| 1 µg/kg (10) | 4.90 ± 1.67 [60] | 3.60 ± 1.20 [60] |
| 10 µg/kg (10) | 4.70 ± 1.62 [80] | 5.20 ± 2.09 [60] |
| 100 µg/kg (10) | 6.20 ± 1.22 [100$^\beta$] | 3.20 ± 0.74 [80] |
| Control Group (10) | 5.70 ± 0.93 [100] | 4.50 ± 1.00 [90] |
| Ondansetron | | |
| 0 µg/kg (10) | 2.70 ± 0.92$^a$ [70] | 1.90 ± 0.66$^a$ [60] |
| 1 µg/kg (10) | 4.80 ± 1.03 [80] | 3.40 ± 0.99 [70] |
| 10 µg/kg (10) | 5.60 ± 2.37 [60] | 4.30 ± 1.71 [50] |
| 100 µg/kg (10) | 6.00 ± 0.70 [100] | 4.80 ± 1.38 [100$^\alpha$] |
| Control Group (12) | 6.36 ± 01.82 [100] | 5.91 ± 1.16 [100$^a$] |
| YM - 060 | | |
| 0 µg/kg (12) | 2.91 ± 1.00 [64] | 1.73 ± 0.56$^b$ [55] |
| 0.01 µg/kg (12) | 3.55 ± 0.64 [91] | 3.27 ± 0.69 [91] |
| 0.1 µg/kg (12) | 3.09 ± 0.86 [73] | 2.09 ± 0.62 [64] |
| 1 µg/kg (12) | 4.82 ± 1.30 [82] | 4.00 ± 1.05 [82] |
| 10 µg/kg (12) | 6.00 ± 1.67 [91] | 3.73 ± 1.03 [82] |
| Control Group (10) | 6.90 ± 0.97 [100] | 5.30 ± 1.07 [100$^\alpha$] |
| FK1052 | | |
| 0 µg/kg (10) | 2.20 ± 0.71$^b$ [70] | 1.30 ± 0.45$^b$ [60] |
| 0.1 µg/kg (10) | 3.80 ± 0.85 [90] | 2.90 ± 0.75 [80] |
| 1 µg/kg (10) | 6.10 ± 1.77 [90] | 4.00 ± 1.41 [70] |
| 10 µg/kg (10) | 5.70 ± 1.18 [100] | 4.40 ± 1.48 [80] |

$^a$P < 0.05, $^b$P < 0.01 vs Control Group (Student's t - test)
$^A$P < 0.01 vs 0 µg/kg (Dunnett's test)
$^\alpha$P < 0.05, $^\beta$P < 0.01 vs 0 µg/kg (Fisher's exact probability test)

Since individual housing completely deprives the male mice of social stimulation, this model is considered to be one of the established psychosocial stress models. As shown in Table 1, the two copulatory elements, mounting and intromission, in individually-housed male mice were significantly depressed than those in group-housed control mice. All the six 5HT$_3$ antagonists tested herein exerted a curative effect on copulatory disorder induced by psychosocial stress. Consequently, it is expected that 5HT$_3$ antagonists have a curative or an ameliorating effect on various stress-induced diseases, for example, male sexual disorder such as impotence and bradyspermatism, and women's dyspareunia and frigidity; eating disorder such as hyperphagia and apastia; digestive disorders such as gastric erosion and gastric ulcer; sleep disorder such as sleeplessness; mental disorder such as melancholia and maternity blue;

equivocal complaint; circular system disorder such as stress-induced hypertension; and any other various stress-induced diseases.

A formulation of the medicine of the invention is exemplified below.

Example 1 (capsules):

| | |
|---|---|
| FK1052 | 5 mg |
| Lactose | 80 mg |

These were mixed and encapsulated into a commonly used hard gelatin capsule.

Advantages of the Invention:

From the test results hereinabove, it is understood that $5HT_3$ antagonist exerts an extremely excellent restoring effect on copulatory disorder induced by psychosocial stress, and are useful as a therapeutic agent for impotence for human being and animals.

We claim:

1. A method for treating impotence which comprises administering an effective amount of a $5HT_3$ antagonist.

* * * * *